United States Patent
Yen et al.

(10) Patent No.: US 10,636,977 B2
(45) Date of Patent: Apr. 28, 2020

(54) LIGHT EMITTING MATERIAL FOR ORGANIC ELECTROLUMINESCENCE DEVICE

(71) Applicants: Feng-Wen Yen, Taipei (TW); Cheng-Hao Chang, Miaoli (TW)

(72) Inventors: Feng-Wen Yen, Taipei (TW); Cheng-Hao Chang, Miaoli (TW)

( * ) Notice: Subject to any disclaimer, the term of this patent is extended or adjusted under 35 U.S.C. 154(b) by 426 days.

(21) Appl. No.: 15/487,436

(22) Filed: Apr. 14, 2017

(65) Prior Publication Data
US 2018/0301631 A1    Oct. 18, 2018

(51) Int. Cl.
| | |
|---|---|
| *H01L 51/54* | (2006.01) |
| *C09K 11/06* | (2006.01) |
| *H01L 51/00* | (2006.01) |
| *C07D 519/00* | (2006.01) |
| *H01L 51/50* | (2006.01) |

(52) U.S. Cl.
CPC ........ H01L 51/0052 (2013.01); *C07D 519/00* (2013.01); *C09K 11/06* (2013.01); *H01L 51/006* (2013.01); *H01L 51/0054* (2013.01); *H01L 51/0055* (2013.01); *H01L 51/0056* (2013.01); *H01L 51/0058* (2013.01); *H01L 51/0094* (2013.01); *C09K 2211/1011* (2013.01); *C09K 2211/1029* (2013.01); *C09K 2211/1096* (2013.01); *H01L 51/0071* (2013.01); *H01L 51/0072* (2013.01); *H01L 51/0073* (2013.01); *H01L 51/0074* (2013.01); *H01L 51/5012* (2013.01); *H01L 2251/5384* (2013.01)

(58) Field of Classification Search
CPC .. C07D 519/00; C09K 11/06; C09K 2211/00; C09K 2211/10; C09K 2211/1007; C09K 2211/1011; C09K 2211/1029; C09K 2211/1096; H01L 51/0032; H01L 51/005; H01L 51/0052; H01L 51/0054; H01L 51/0055; H01L 51/0056; H01L 51/0058; H01L 51/006; H01L 51/0071; H01L 51/0072; H01L 51/0073; H01L 51/0074; H01L 51/5012
USPC ....... 428/690, 691, 917, 411.4, 336; 427/58, 427/66; 313/500–512; 257/40, 88–104; 257/E51.001–E51.052; 252/301.16–301.35
See application file for complete search history.

(56) References Cited

U.S. PATENT DOCUMENTS

| | | | |
|---|---|---|---|
| 6,447,934 B1 * | 9/2002 | Suzuki | H01L 51/5036 257/103 |
| 9,000,171 B2 | 4/2015 | Itoi et al. | |
| 2012/0168730 A1 | 7/2012 | Kim et al. | |
| 2012/0206035 A1 * | 8/2012 | Shitagaki | H01L 51/0072 313/503 |
| 2012/0248968 A1 | 10/2012 | Ogiwara et al. | |
| 2014/0175383 A1 * | 6/2014 | Yen | H01L 51/0058 257/40 |
| 2016/0130225 A1 * | 5/2016 | Tasaki | C07D 209/80 257/40 |

FOREIGN PATENT DOCUMENTS

KR    20130069439 A  *  6/2013

OTHER PUBLICATIONS

Machine translation of KR2013-0069439. (Year: 2013).*

* cited by examiner

*Primary Examiner* — Andrew K Bohaty

(57) ABSTRACT

A light emitting material is represented by the following formula (1), the organic EL device employing the material as delayed fluorescence emitting dopant or fluorescence emitting dopant can display good performance like as lower driving voltage and power consumption, especially doping with the host (H1 to H4) and the second host (SH1 to SH4) can increasing efficiency and half-life time.

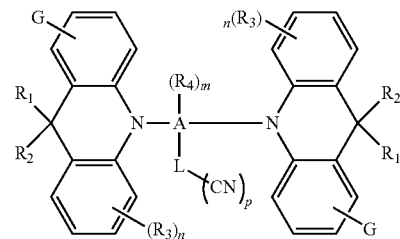

formula(1)

wherein G represents the following formula (2):

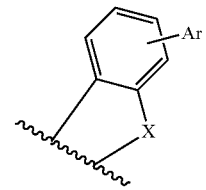

formula(2)

L, m, n, p, $R_1$ to $R_4$, Ar and X are the same definition as described in the present invention.

9 Claims, 1 Drawing Sheet

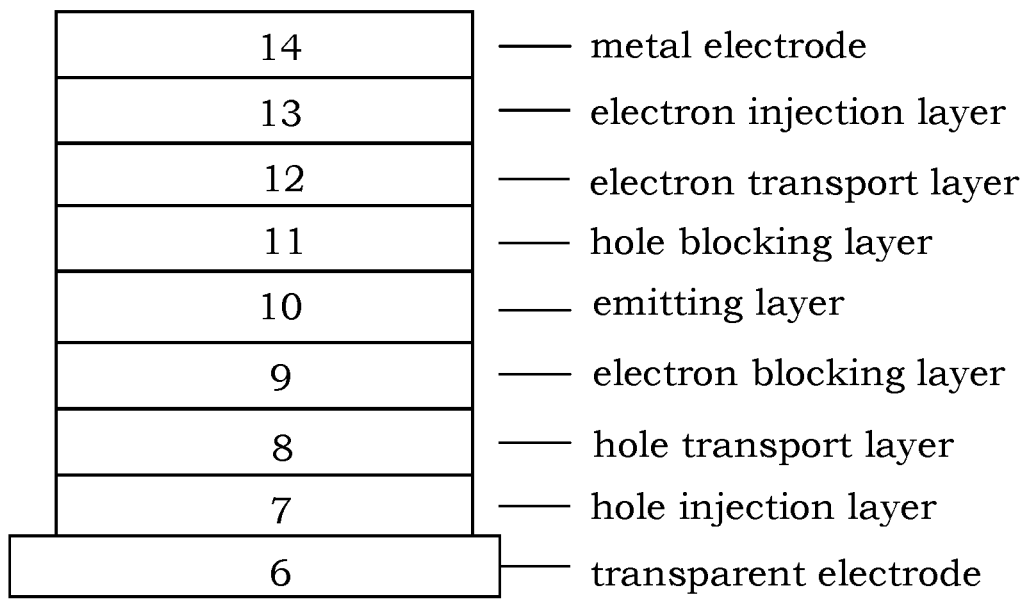

LIGHT EMITTING MATERIAL FOR ORGANIC ELECTROLUMINESCENCE DEVICE

FIELD OF INVENTION

The present invention relates to a light emitting material and organic electroluminescence (herein referred to as organic EL) device using the light emitting material having general formula (1), and an organic EL device employing the light emitting material as delayed fluorescence emitting dopant or fluorescence emitting dopant of emitting layer can display good performance.

BACKGROUND OF THE INVENTION

Organic electroluminescence (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden. Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC).

For full-colored flat panel displays in AMOLED the material used for the blue fluorescent emitting layer are still unsatisfactory in half-life time, efficiency and driving voltage. In the present invention, for the purpose to prolong the half-life time and lower driving voltage for fluorescent dopant in emitting layer for organic EL device, we employ a acridine-based hererocyclic skeleton link to a cyano group substituted naphthyl group, phenanthrenyl group, anthracenyl group, pyrenyl group, chrysenyl group, triphenylenyl group and perylenyl group to finish the light emitting material represented as general formula (1). The light emitting material show good thermal stability and charge carrier mobility for organic EL device. Acridine-based hererocyclic skeleton based derivative disclosed in WO 2006033563A1, US20120168730 A1, US20120248968A1, US9000171B2 are used for organic EL device are described. There are no prior arts demonstrate a acridine-based hererocyclic skeleton link to a cyano group substituted naphthyl group, phenanthrenyl group, anthracenyl group, pyrenyl group, chrysenyl group, triphenylenyl group and perylenyl group used as delayed fluorescence emitting dopant or fluorescence emitting dopant for organic EL device.

According to the reasons described above, the present invention has the objective of resolving such problems of the prior-art and offering a light emitting device which is excellent in its thermal stability, high luminance efficiency, high luminance and long half-life time. The present invention disclose a light emitting material having general formula (1), used as a delayed fluorescence emitting dopant or fluorescent emitting dopant material have good charge carrier mobility and excellent operational durability can lower driving voltage and power consumption, increasing efficiency and half-life time of organic EL device.

SUMMARY OF THE INVENTION

In accordance with the present invention, the light emitting material and their use for delayed fluorescence dopant or fluorescent dopant of emitting layer for organic EL device are provided. The light emitting material can overcome the drawbacks of the conventional materials like as shorter half-life time, lower efficiency and higher driving voltage.

An object of the present invention is to apply the light emitting material as fluorescent emitting dopant for organic EL device and can lower driving voltage, lower power consumption and increase the efficiency.

An object of the present invention is to apply the light emitting material as delayed fluorescent emitting dopant or co-deposited with the host and the second fluorescence host for organic EL device can increase the efficiency and half-life time.

The present invention has the economic advantages for industrial practice. Accordingly, the present invention discloses the light emitting material which can be used for organic EL device is disclosed. The mentioned the light emitting material is represented by the following formula (1)

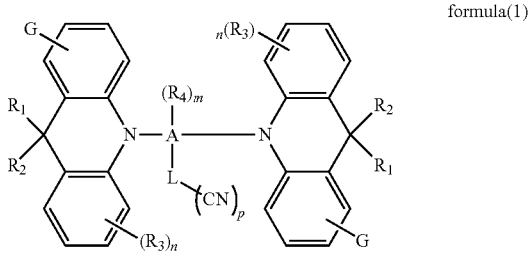

formula(1)

wherein G represents the following formula (2):

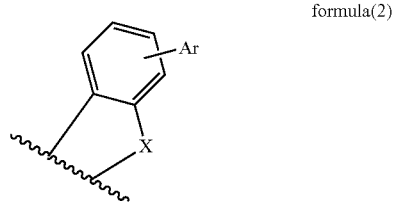

formula(2)

A represents a fused ring hydrocarbon units with two to five rings, provided A represents a naphthyl group, a phenanthrenyl group, a anthracenyl group, a pyrenyl group, a chrysenyl group, a triphenylenyl group and a perylenyl group; L represents a single bond, a substituted or unsubstituted phenylene group or a substituted or unsubstituted heterophenylene group, X represents a divalent bridge selected from the atom or group consisting from O, S, $C(R_5)(R_6)$, $Si(R_7)(R_8)$ and $N(R_9)$, Ar represents a fused carbocyclic ring or $R_1$, m represents an integer of 0 to 10, n represents an integer of 0 to 4, p represents an integer of 0 to 4, $R_1$ to $R_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

BRIEF DESCRIPTION OF THE DRAWINGS

The FIGURE shows one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is fluorescence emitting layer which is deposited onto 9, 11 is hole blocking layer which is deposited onto 10, 12 is electron transport layer which is deposited on to 11, and 13 is electron injection layer which is deposited on to 12.

DESCRIPTION OF THE PREFERRED EMBODIMENTS

What probed into the invention is the light emitting material and organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims In a first embodiment of the present invention, the light emitting material which can be used as delayed fluorescence emitting dopant or fluorescent emitting dopant for organic EL device are disclosed. The mentioned light emitting material represented by the following formula (1):

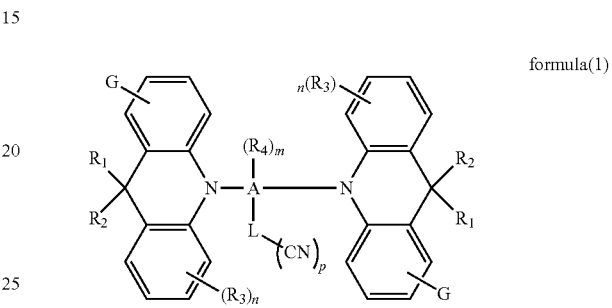

formula(1)

wherein G represents the following formula (2):

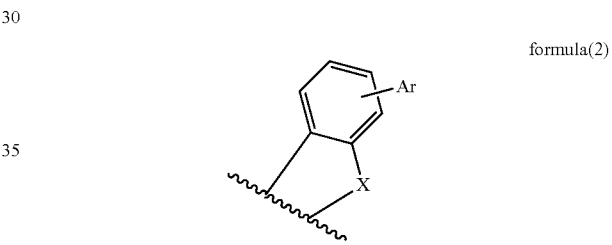

formula(2)

A represents a fused ring hydrocarbon units with two to five rings, provided A represents a naphthyl group, a phenanthrenyl group, a anthracenyl group, a pyrenyl group, a chrysenyl group, a triphenylenyl group and a perylenyl group; L represents a single bond, a substituted or unsubstituted phenylene group or a substituted or unsubstituted heterophenylene group, X represents a divalent bridge selected from the atom or group consisting from O, S, $C(R_5)(R_6)$, $Si(R_7)(R_8)$ and $N(R_9)$, Ar represents a fused carbocyclic ring or $R_1$, m represents an integer of 0 to 10, n represents an integer of 0 to 4, p represents an integer of 0 to 4, $R_1$ to $R_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

According to the above-mentioned the light emitting material formula (1), wherein A is represented by the following formulas:

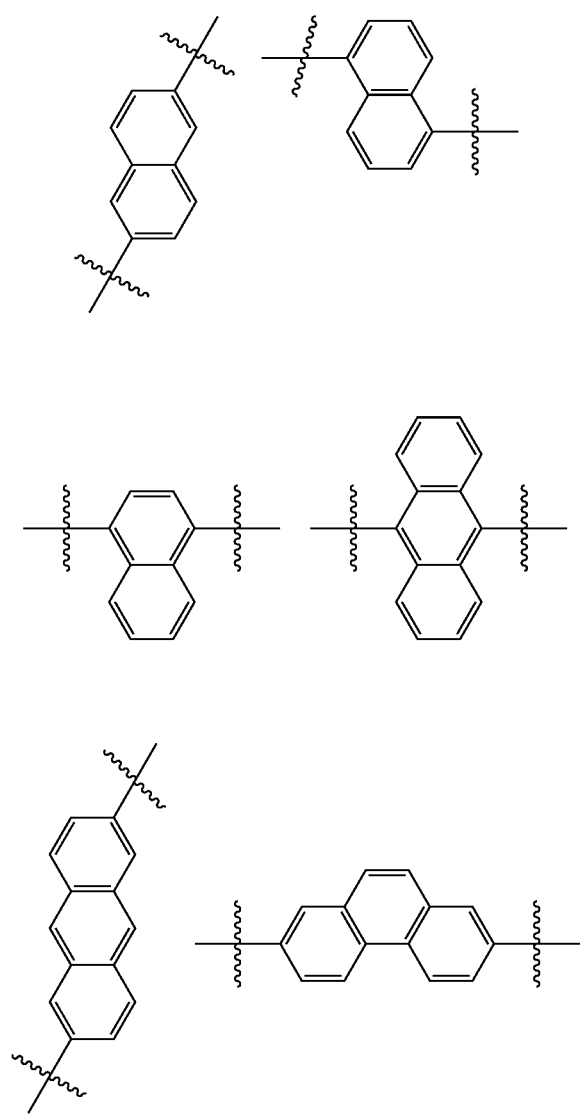
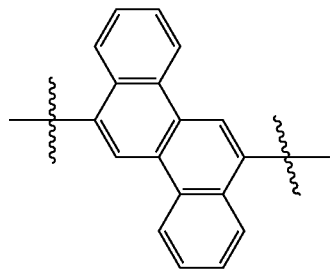
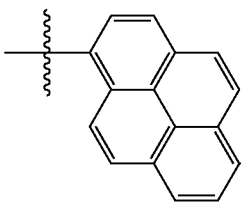
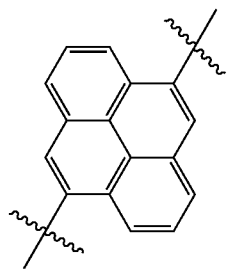
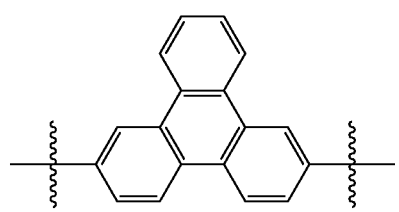
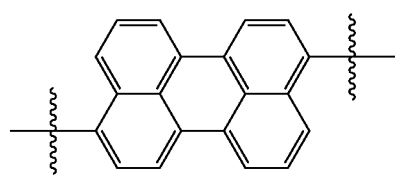
In this embodiment, some light emitting material are shown below:
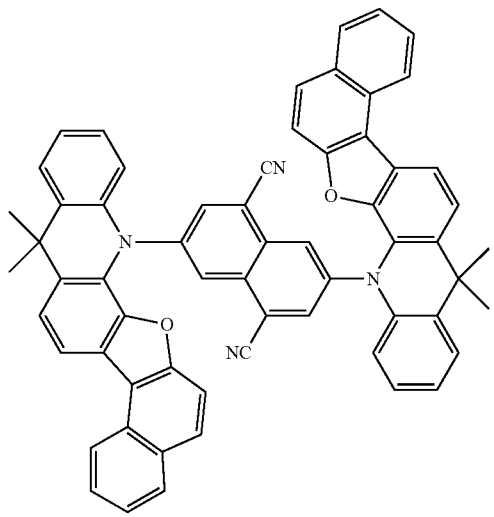
C1
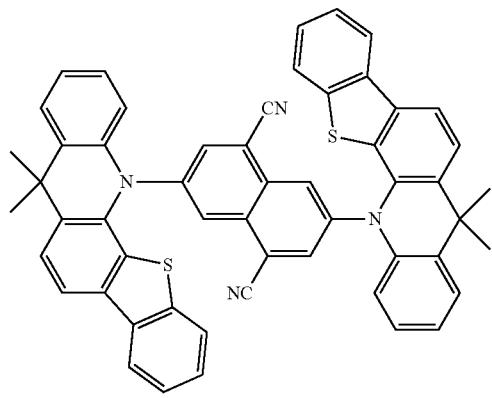
C2

-continued
C3
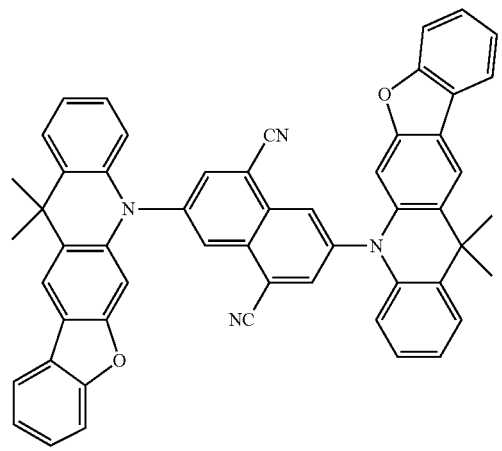
C4
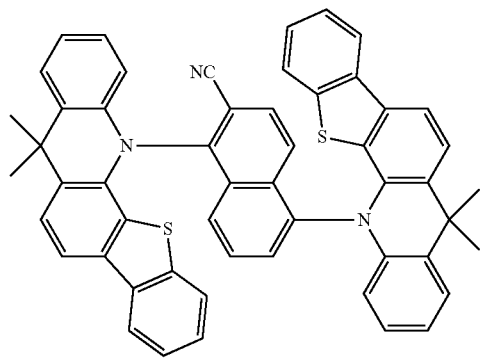
C5
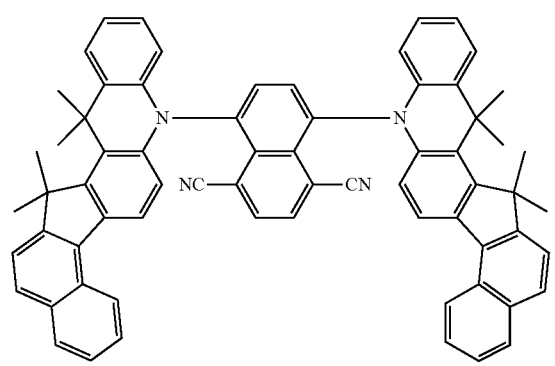
C6
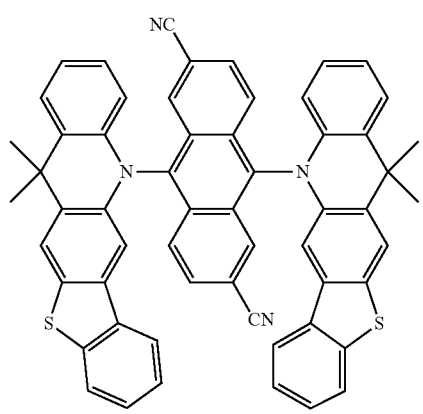
C7
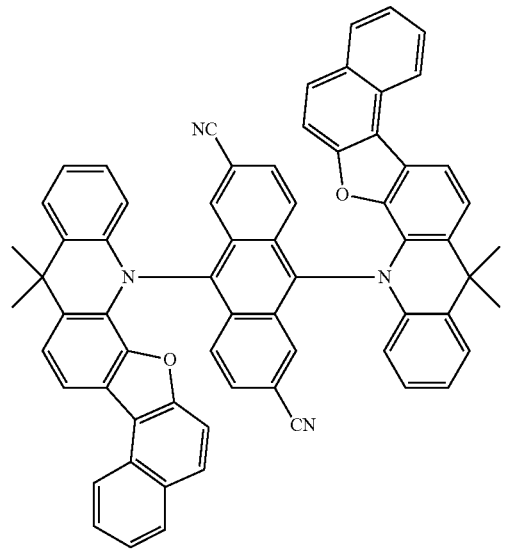
C8
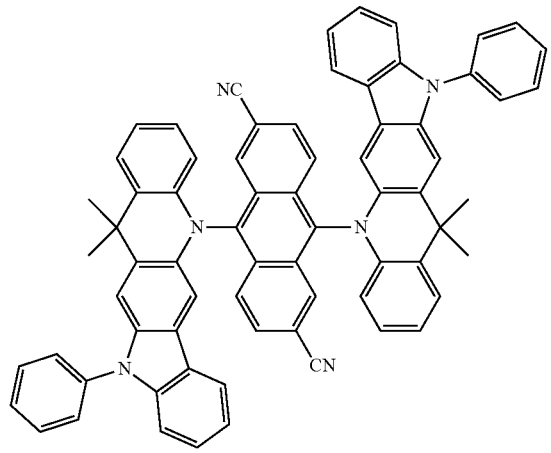

-continued
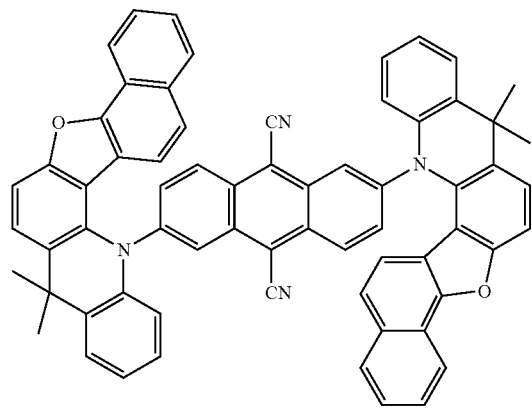
C9
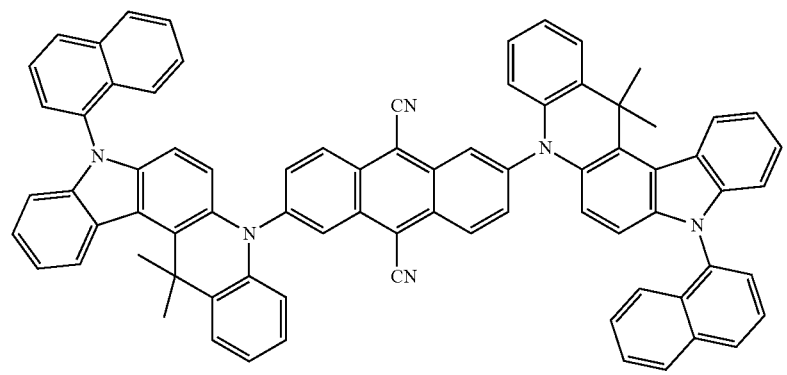
C10
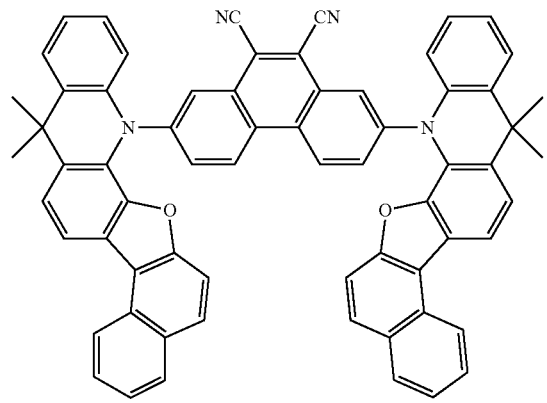
C11
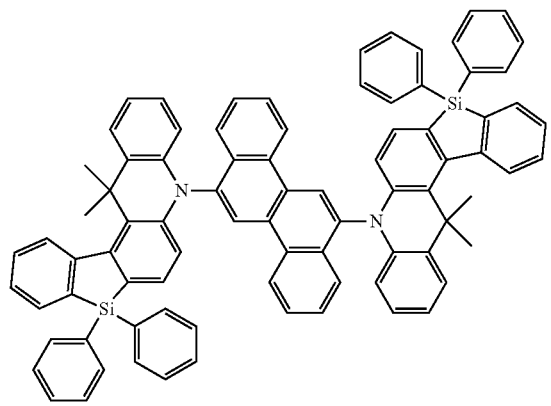
C12

-continued
C13
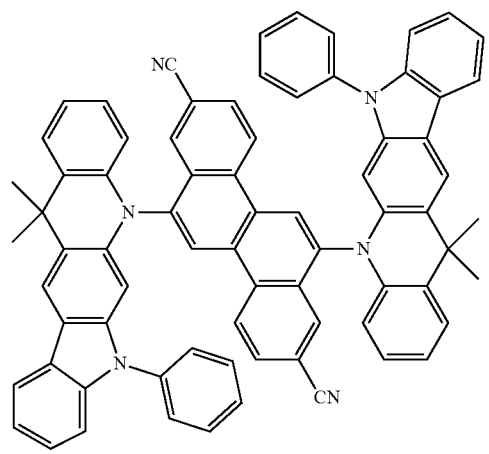
C14
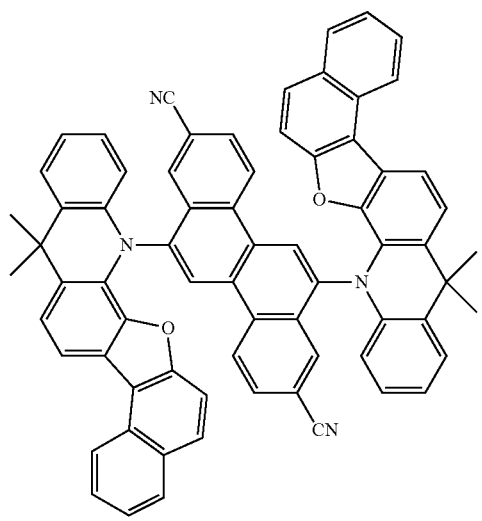
C15
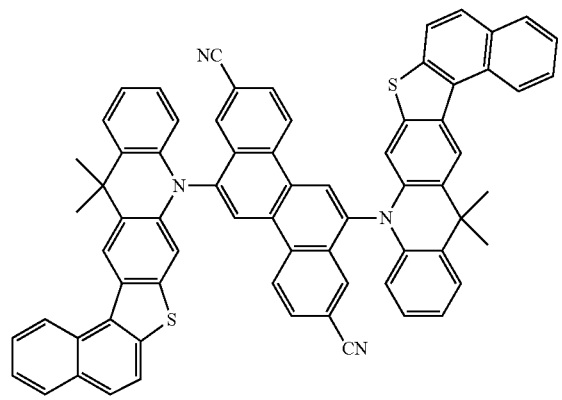
C16
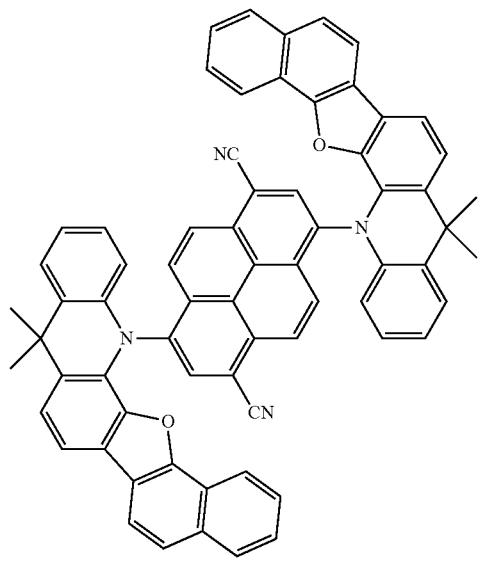
C17
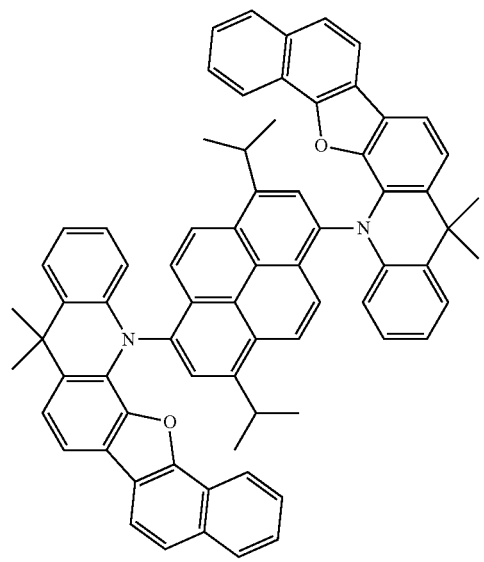
C18
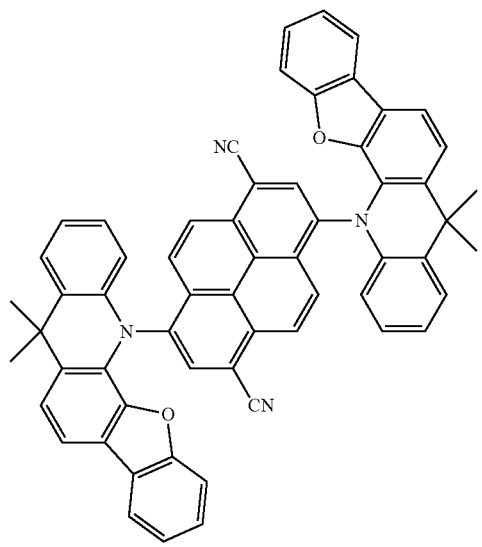

-continued
C19
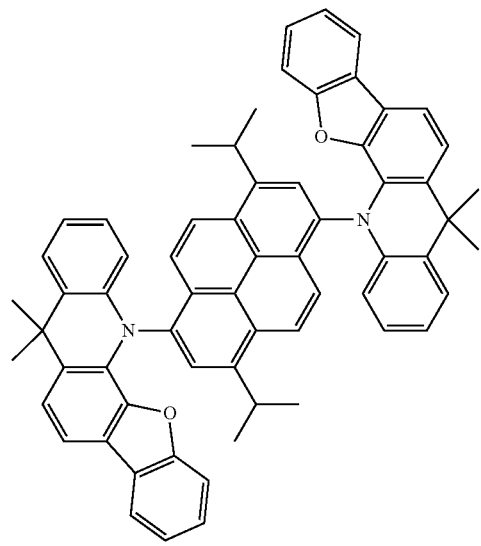
C20
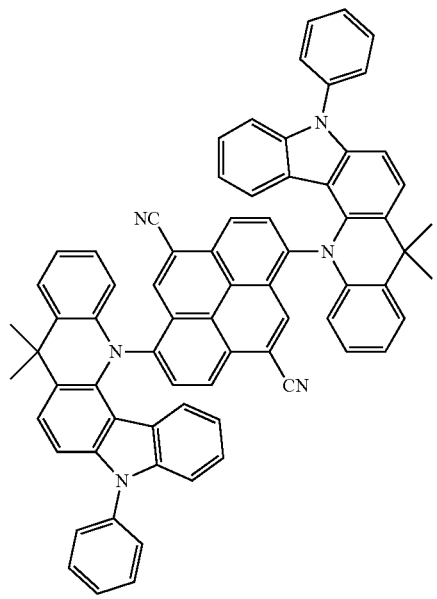
C21
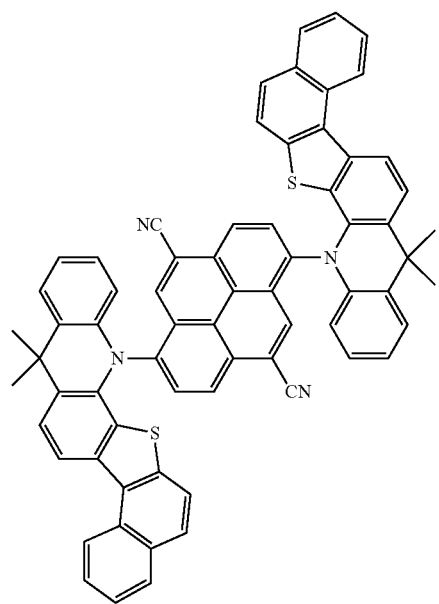
C22
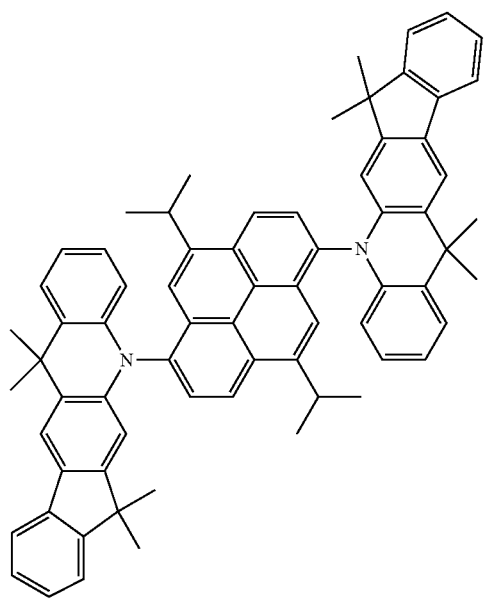

C23

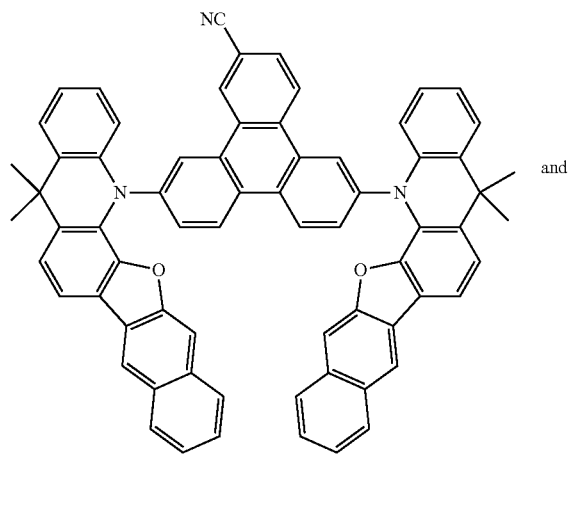

and

C24

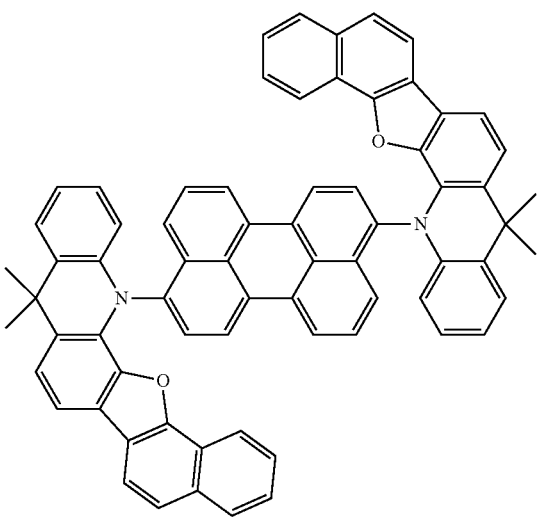

Detailed preparation for the light emitting material in the present invention could be clarified by exemplary embodiments, but the present invention is not limited to exemplary embodiments. EXAMPLE 1-4 show the preparation for examples of the organic material in the present invention. EXAMPLE 5 shows the fabrication of organic EL device and I-V-B, half-life time of organic EL device testing report.

Example 1

Synthesis of C16

Synthesis of 2-bromo-6-(naphthalen-2-yl)phenol

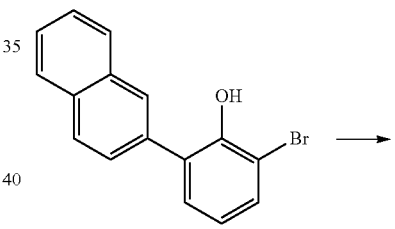

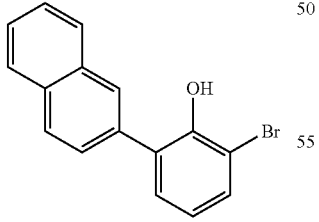

A mixture of 39.5 g (157 mmol) of 2,6-dibromophenol, 27.0 g (157 mmol) of naphthalen-2-ylboronic acid, 3.5 g (3 mmol) of Pd(PPh$_3$)$_4$, 157 ml of 2M Na$_2$CO$_3$, 200 ml of EtOH and 400 ml of toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica gel to give product (27.2 g, 91 mmol, 58%) as a white solid.

Synthesis of 10-bromobenzo[d]naphtho[1,2-b]furan

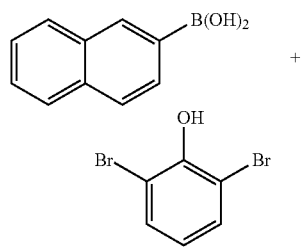

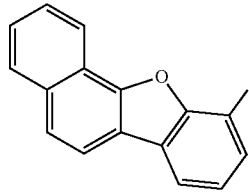

A mixture of 27.2 g (91 mmol) of 2-bromo-6-(naphthalen-2-yl) phenol, 2.2 g (9.7 mmol) of Pd(OAc)$_2$, 1.2 g (9.7 mmol) of 3-nitropyridine, 37.5 g (193 mmol) of tert-butyl peroxybenzoate, 150 ml of C$_6$F$_6$ and 100 ml of DMF was degassed and placed under nitrogen, and then heated at 150° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica gel to give product (11 g, 37.3 mmol, 41%) as a white solid.

Synthesis of methyl 2-(benzo[d]naphtho[1,2-b]furan-10-ylamino) Benzoate

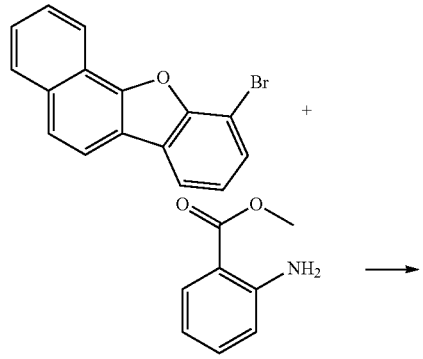

A mixture of 14.9 g (50 mmol) 10-bromobenzo[d]naphtho[1,2-b] furan, 8.3 g (55 mmol) of methyl 2-aminobenzoate, 0.25 g (1 mmol) of palladium (II) acetate, 0.75 g (2.0 mmol) of 2-(dicyclohexylphosphino)biphenyl, 9.6 g (100 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give product (9.4 g, 25.5 mmol, 51%) of yellow product which was recrystallized from hexane.

Synthesis of 2-(2-(benzo[d]naphtho[1,2-b]furan-10-ylamino) phenyl)propan-2-ol

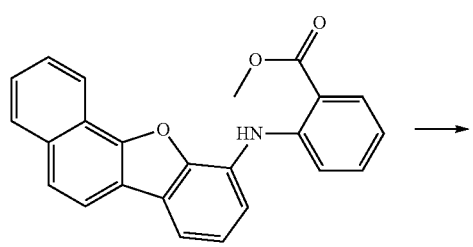

33.4 g (91 mmol) of methyl 2-(benzo[d]naphtho[1,2-b] furan-10-yl amino) benzoate was placed in a flask, and the flask was made vacuous and filled with N$_2$. 700 ml of tetrahydrofuran was added, stirring was performed at –78° C. 10 minutes. Subsequently, 284 ml (455 mol) of MeLi (1.6M in hexane) was added thereto, stirred at –78° C. for 10 minutes, and stirred at room temperature for 6 hours. After termination of the reaction, the reaction product was extracted with distilled water and ethyl acetate. The resultant organic layer was dried with MgSO$_4$, evaporated using a rotary evaporator to remove the solvent, and subjected to column chromatography using hexane and ethyl acetate as a developing solvent, thus obtaining 26 g (71 mmol, 78%) of 2-(2-(benzo[d]naphtha [1,2-b]furan-10-ylamino)phenyl) propan-2-ol Synthesis of Intermediate I

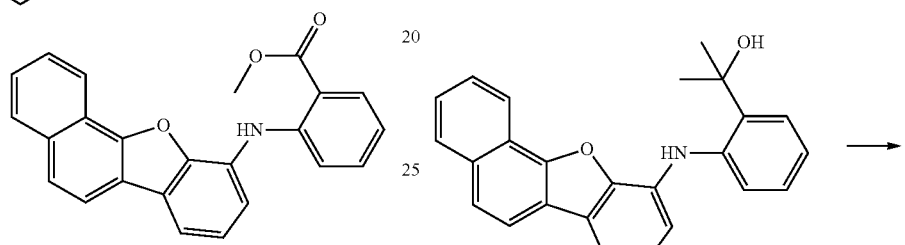

Intermediate I 26 g (71 mmol) of 2-(2-(benzo[d]naphtho[1,2-b]furan-10-ylamino) rated using a rotary evaporator to remove the solvent, and subjected to column chromatography using hexane and ethyl acetate as a developing solvent, thus phenyl)propan-2-ol was placed in a flask, and the flask was made vacuous and filled with N$_2$. 200 ml of AcOH was added, stirring was performed at 0° C. 10 minutes. The reaction mixture was added with 400 ml of H$_3$PO$_4$ and stirred at room temperature for 3 hour. After termination of the reaction, the reaction product was neutralized with NaOH, and extracted with distilled water and ethyl acetate. The resultant organic layer was dried with MgSO4, obtaining 18.4 g (74%) of intermediate I.

Synthesis of pyrene-1,6-dicarbonitrile

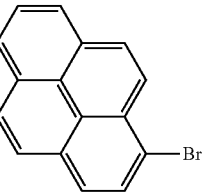

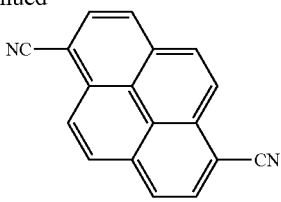

30 g of 1,6-dibromopyrene was diluted in 600 ml of dimethylformamide, and then, 20 g of CuCN was dropped thereto, and the mixture was refluxed at a temperature of 170° C. while stirring. After termination of the reaction, the temperature was cooled to room temperature, water was used to stop the reaction, and extracted with water and ethyl acetate. The resultant organic layer was dried with MgSO4, evaporated using a rotary evaporator to remove the solvent, and subjected to column chromatography using hexane and ethyl acetate as a developing solvent, thus obtaining (19.6 g, 77.5 mmol, 93%) of pyrene-1,6-dicarbonitrile Synthesis of 3,8-dibromopyrene-1,6-dicarbonitrile

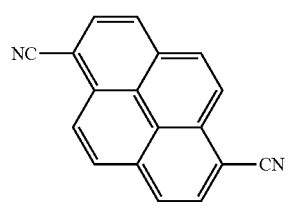  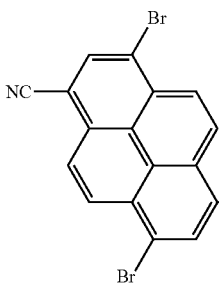

The resulting pyrene-1,6-dicarbonitrile (19.6 g, 77.7 mmol) and DMF (300 ml) were added to a reaction vessel. N-bromosuccinimide (33 g, 186 mmol) was added under ice-cooled conditions, and the mixture was stirred for 9 hours. The precipitated crystal was separated by filtration and washed with water and methanol, to give product (13.1 g, 31.8 mmol, 41%) as a yellow solid.

Synthesis of C16

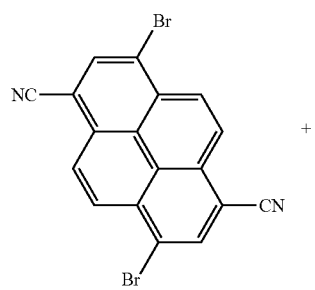

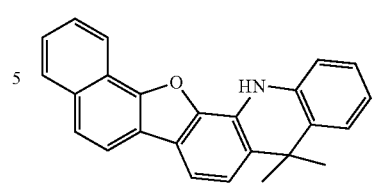

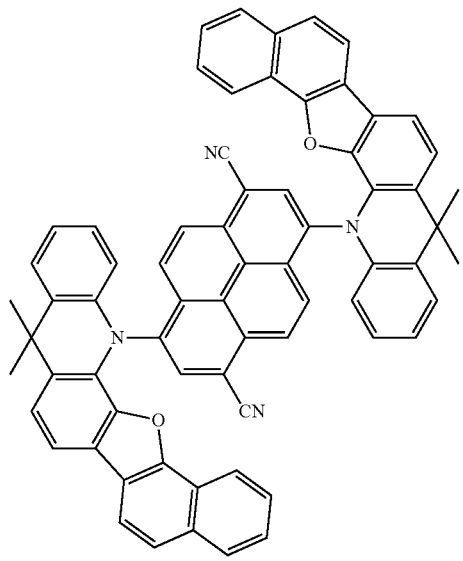

A mixture of 4.1 g 10 mmol) 3,8-dibromopyrene-1,6-dicarbonitrile, 7.1 g (20.4 mmol) of intermediate I, 0.05 g (0.2 mmol) of palladium (II)acetate, 0.15 g (0.4 mmol) of 2-(dicyclohexylphosphino)biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 6.4 g (yield 61%) of yellow product which was recrystallized from toluene and purified by vacuum sublimation. MS (m/z, FAB⁻): 946.3.

Example 2

Synthesis of C17

Synthesis of 1,6-diisopropylpyrene

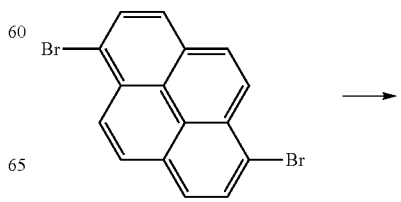

Synthesis of C17

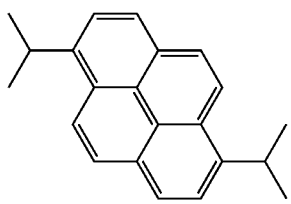

In a 1 L round-bottom three-neck flask, 20 g (55.6 mmol) of 1,6-dibromopyrene, 120 ml of 1M isopropylmagnesium-bromide, 2.3 g of (diphenylphosphinoferrocene)palladium (II) dichloride and 200 ml of dried dioxane were placed into flask and the resultant solution was stirred with heating at a temperature of 100° C. for 24 hours. After the completion of the reaction, adding 100 ml of dilute hydrochloric acid, an organic layer was separated and concentrated under a reduced pressure. Then, the organic layer was passed through a silica gel short column, and after concentrating under the reduced pressure again, a precipitated crystal was separated by filtration and as a result, 6.2 g of 1,6-diisopropylpyrene was obtained (yield 39%).

Synthesis of 1,6-dibromo-3,8-diisopropylpyrene

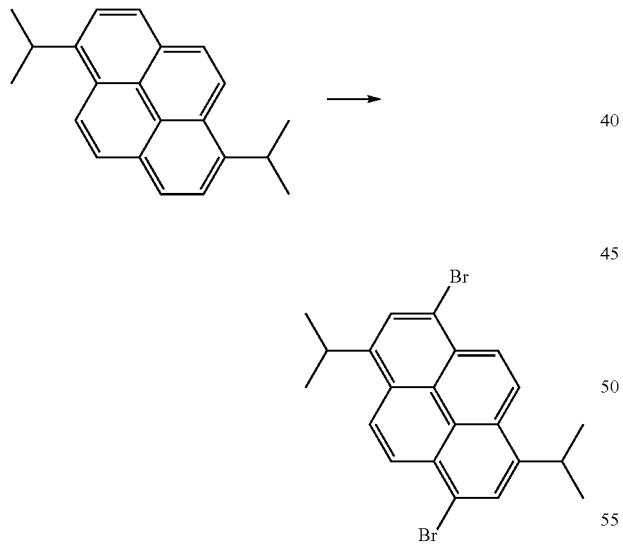

The resulting 1,6-diisopropylpyrene (22.3 g, 77.7 mmol) and DMF (300 ml) were added to a reaction vessel. N-bromosuccinimide (33 g, 186 mmol) was added under ice-cooled conditions, and the mixture was stirred for 9 hours. The precipitated crystal was separated by filtration and washed with water and methanol, to give product (9.7 g, 21.8 mmol, 28%) as a yellow solid.

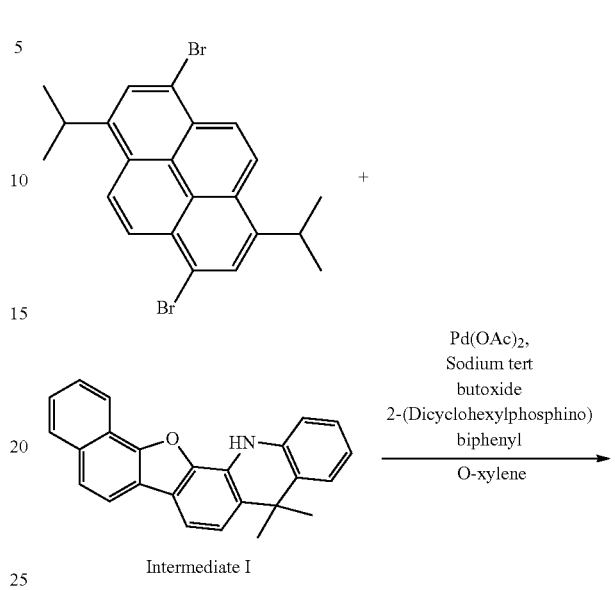

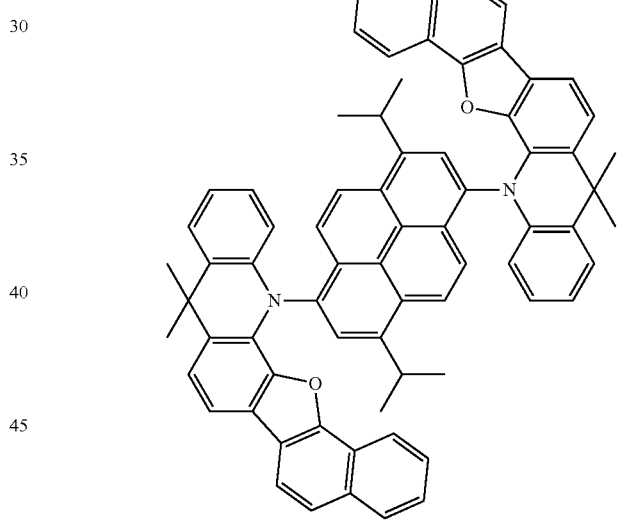

A mixture of 4.4 g (10 mmol) 1,6-dibromo-3,8-diisopropylpyrene, 7.1 g (20.4 mmol) of intermediate I, 0.05 g (0.2 mmol) of palladium (II) acetate, 0.15 g (04 mmol) of 2-(dicyclohexylphosphino)biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 4.6 g (yield 47%) of yellow product which was recrystallized from toluene and purified by vacuum sublimation. MS (m/z, FAB+):980.5.

Example 3

Synthesis of C18

Synthesis of methyl 2-(dibenzo[b,d]furan-4-ylamino)benzoate

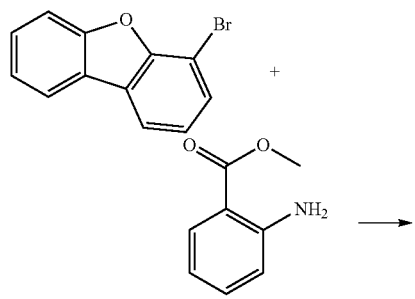

A mixture of 12.4 g (50 mmol) 4-bromodibenzo[b,d]furan, 8.3 g (55 mmol) of methyl 2-aminobenzoate, 0.25 g (1 mmol) of palladium (II)acetate, 0.75 g (2.0 mmol) of 2-(dicyclohexylphosphino)biphenyl, 9.6 g (100 mmol) of sodium tert-butoxide and 100 ml of o-xylene was refluxed under nitrogen overnight. After finishing the reaction, the solution was filtered at 100° C., to receive the filtrate, and the filtrate was added to 1 L MeOH, while stirring and the precipitated product was filtered off with suction. To give product (14 g, 31.5 mmol, 63%) of yellow product which was recrystallized from hexane.

Synthesis of 2-(2-(dibenzo[b,d]furan-4-ylamino)phenyl)propan-2-ol

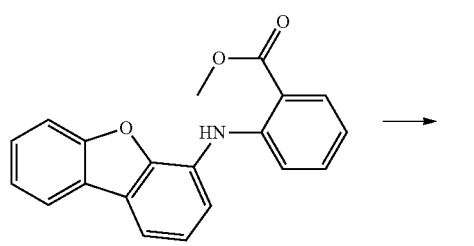

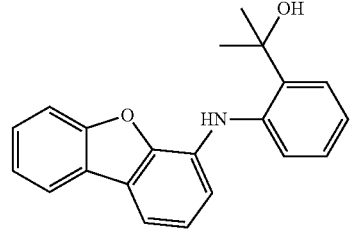

14 g (31.5 mmol) of methyl 2-(dibenzo[b,d]furan-4-ylamino) benzoate was placed in a flask, and the flask was made vacuous and filled with $N_2$. 230 ml of tetrahydrofuran was added, stirring was performed at −78° C. 10 minutes. Subsequently, 95 ml (152 mol) of MeLi (1.6M in hexane) was added thereto, stirred at −78° C. for 10 minutes, and stirred at room temperature for 6 hours. After termination of the reaction, the reaction product was extracted with distilled water and ethyl acetate. The resultant organic layer was dried with $MgSO_4$, evaporated using a rotary evaporator to remove the solvent, and subjected to column chromatography using hexane and ethyl acetate as a developing solvent, thus obtaining 8.5 g (26.8 mmol, 85%) of 2-(2-(dibenzo[b,d]furan-4-ylamino)phenyl)propan-2-ol.

Synthesis of 5,5-dimethyl-5,13-dihydrobenzofuro[3,2-c]acridine

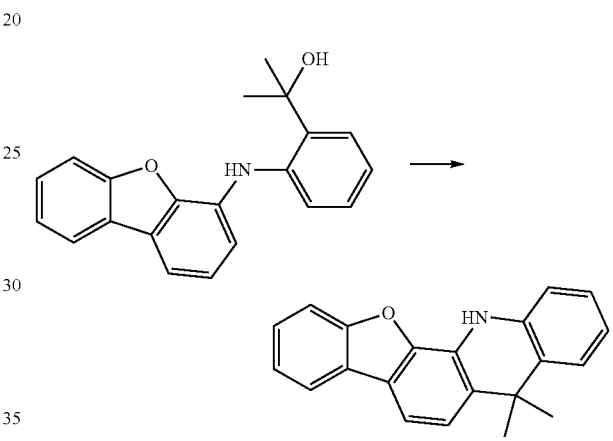

8.5 g (26.8 mmol) of 2-(2-(dibenzo[b,d]furan-4-ylamino) phenyl) propan-2-ol was placed in a flask, and the flask was made vacuous and filled with $N_2$. 70 ml of AcOH was added, stirring was performed at 0° C. 10 minutes. The reaction mixture was added with 130 ml of $H_3PO_4$ and stirred at room temperature for 3 hour. After termination of the reaction, the reaction product was neutralized with NaOH, and extracted with distilled water and ethyl acetate. The resultant organic layer was dried with MgSO4, evaporated using a rotary evaporator to remove the solvent, and subjected to column chromatography using hexane and ethyl acetate as a developing solvent, thus obtaining 6.6 g (83%) of 5,5-dimethyl-5,13-dihydrobenzofuro[3,2-c]acridine.

Synthesis of C18

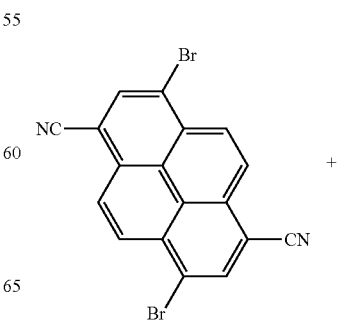

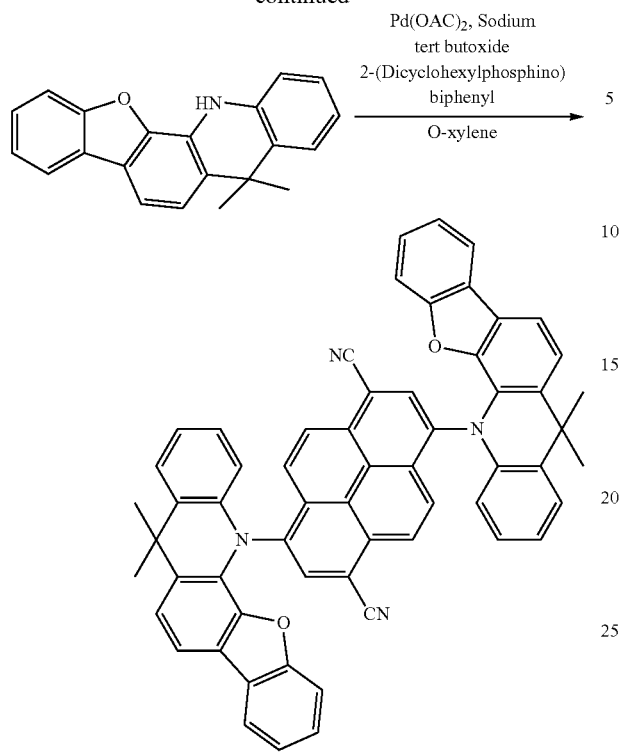

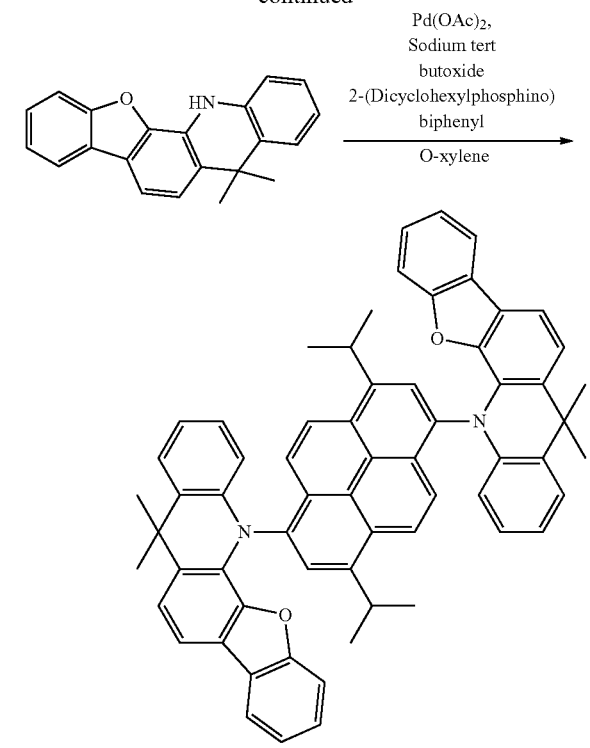

A mixture of 4.1 g (10 mmol) 3,8-dibromopyrene-1,6-dicarbonitrile, 6.1 g (20.4 mmol) of 5,5-dimethyl-5,13-dihydrobenzofuro[3,2-c]acridine, 0.05 g (0.2 mmol) of palladium (II)acetate, 0.15 g (0.4 mmol) of 2-(dicyclohexyl phosphino)biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 4.8 g (yield 57%) of yellow product which was recrystallized from toluene and purified by vacuum sublimation. MS (m/z, FAB+): 846.5.

Example 4

Synthesis of C19

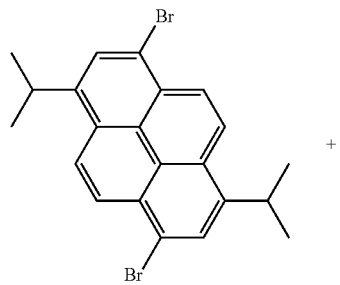

A mixture of 4.4 g (10 mmol) 1,6-dibromo-3,8-diisopropylpyrene, 6.1 g (20.4 mmol) of 5,5-dimethyl-5,13-dihydrobenzofuro[3,2-c]acridine, 0.05 g (0.2 mmol) of palladium (II) acetate, 0.15 g (0.4 mmol) of 2-(dicyclohexylphosphino) biphenyl, 3.8 g (40 mmol) of sodium tert-butoxide and 50 ml of o-xylene was refluxed under nitrogen overnight. After finishing the reaction, the solution was filtered at 120° C., to receive the filtrate, and the filtrate was added to 1 L MeOH, while stirring and the precipitated product was filtered off with suction. To give 5.4 g (yield 62%) of yellow product which was recrystallized from toluene and purified by vacuum sublimation. MS (m/z, FAB+): 880.1.

General Method of Producing Organic EL Device

ITO-coated glasses with 9-12 ohm/square in resistance and 120-160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3f:2,3-]quinoxaline-2,3,6,7,10,11-hexacarbonitrile (HAT-CN) is used as hole injection layer in this organic EL device, and N4,N4'-di(biphenyl-4-yl)-N4,N4'- diphenylbiphenyl-4,4'-diamine (HT1) is used as the hole transporting layer, N-(biphenyl-4-yl)-9,9-dimethyl-N-(4'-phenyl biphenyl-4-yl)-9H-fluoren-2-amine (EB2) is used as electron blocking layer, H1 to H4 are used as fluorescence host, H5 used as delayed fluorescence host and SH1 to SH4 are used as second fluorescence host in the present invention. The chemical structure shown below:

HAT-CN

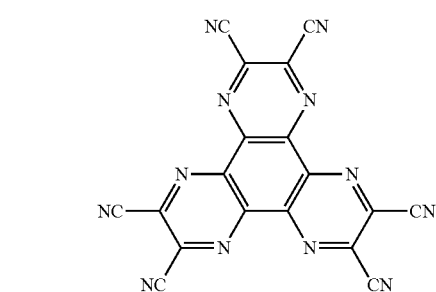

HT1

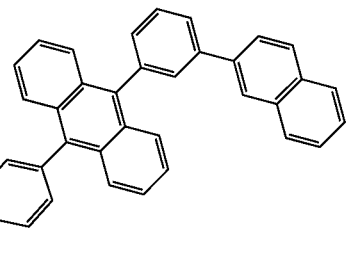

H2

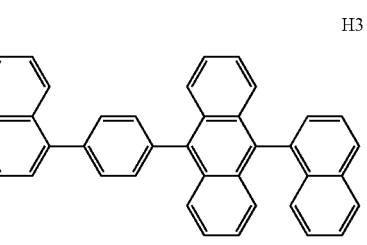

H3

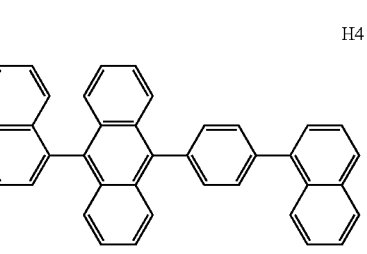

H4

EB2

H1

H5

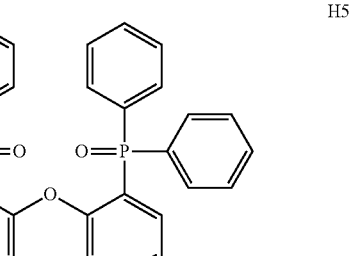

SH1

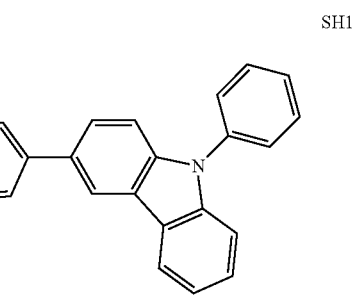

SH2
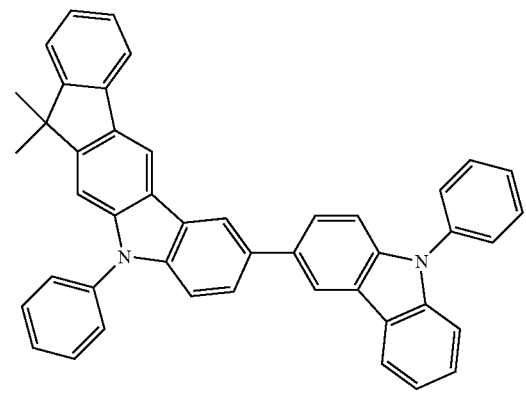
SH3
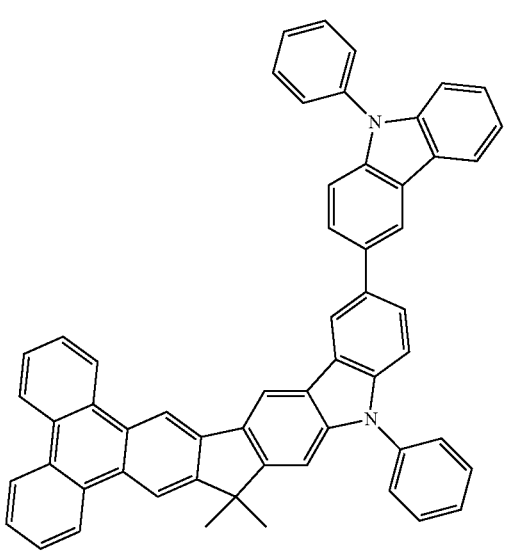
SH4
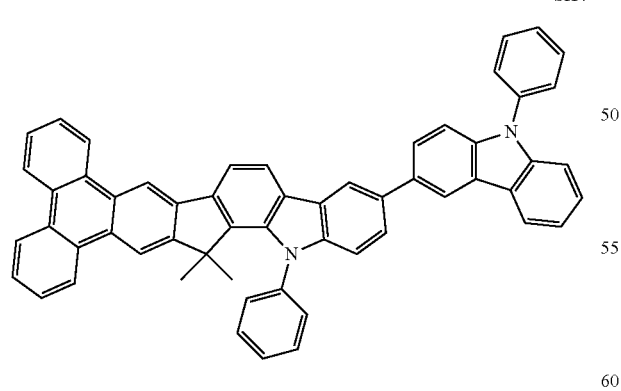
C16
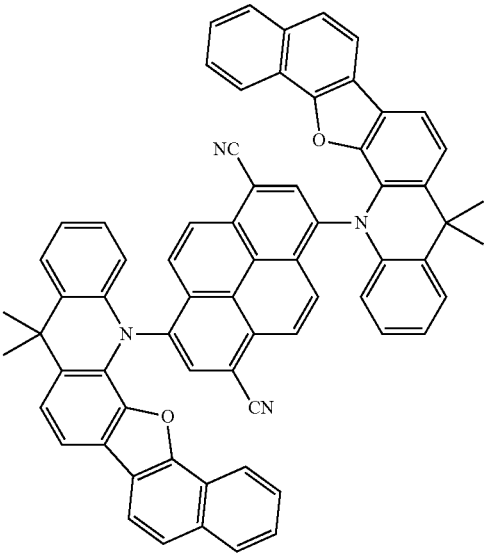
C17
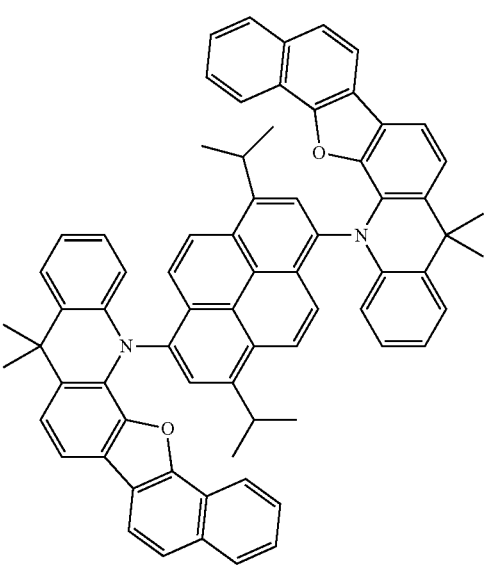
C18
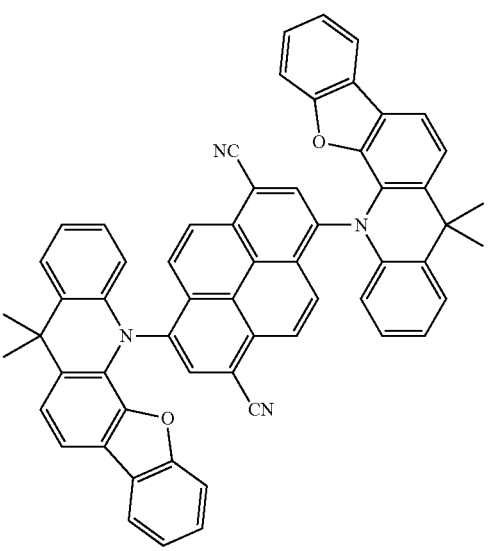
The following light emitting material Examples 1 to Example 4 prepared in the present invention can be verified and used as delayed fluorescence dopant or fluorescence dopant by organic EL device and N1, N1, N6, N6-tetram-tolylpyrene-1,6-diamine (D1) is used as fluorescence blue dopant for comparison.

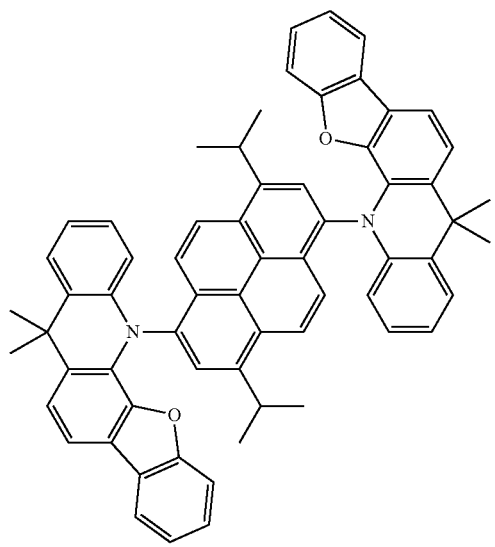

C19

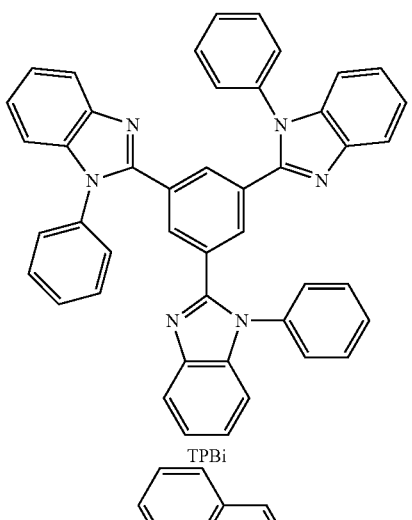

TPBi

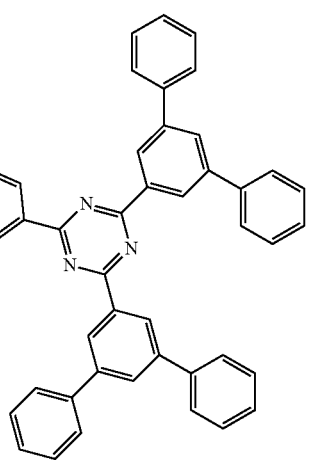

LiQ

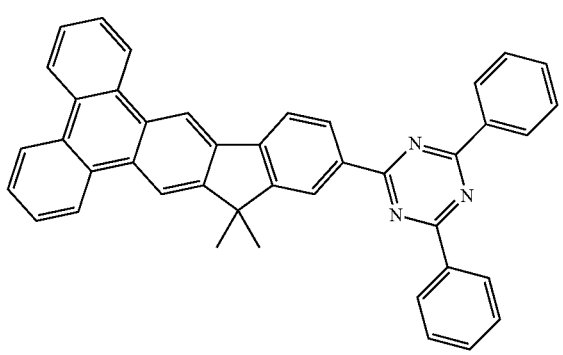

ET2

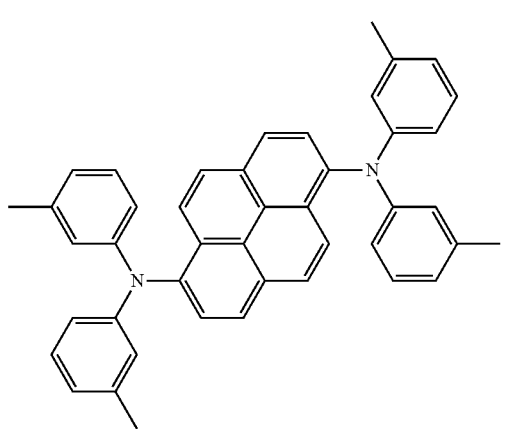

D1

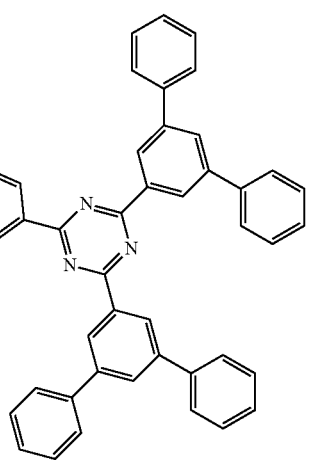

HB3

2,2',2"-(1,3,5-Benzinetriyl)-tris(1-phenyl-1-H-benzimidazole) (TPBi) and HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or Li$_2$O. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 5

Using a procedure analogous to the above mentioned general method, organic fluorescence or delayed fluorescence EL device having the following device structure was produced (See the FIGURE). Device: ITO/HAT-CN(20 nm)/HT1(110 nm)/EB2(5 nm)/Host+3%~15% dopant(30 nm)HBM(10 nm)/ETM doped 40% LiQ(35 nm)/LiQ(1 nm)/Al(160 nm). The I-V-B (at 1000 nits) of organic EL device testing report as Table1. The T$_{70}$ is defined that the initial luminance of 3000 cd/m$^2$ has dropped to 2100 cd/m$^2$.

TABLE 1

| Dopant (%) | Host or cohost (8:2) | HBM | Voltage (V) | Efficiency (cd/A) | Device color | T$_{70}$ |
| --- | --- | --- | --- | --- | --- | --- |
| C16 (5%) | H1 | HB3 | 4.5 | 5.0 | Blue | 220 |
| C17 (5%) | H2 | HB3 | 4.5 | 4.8 | Blue | 195 |
| C18 (5%) | H1 | HB3 | 5.0 | 5.1 | Blue | 210 |
| C19 (5%) | H2 | HB3 | 5.1 | 5.8 | Blue | 230 |
| C16 (5%) | H3 | HB3 | 4.6 | 5.2 | Blue | 225 |
| C17 (5%) | H4 | HB3 | 4.8 | 5.0 | Blue | 215 |
| C18 (5%) | H3 | HB3 | 4.5 | 5.2 | Blue | 185 |
| C19 (5%) | H4 | HB3 | 5.0 | 5.5 | Blue | 205 |
| D1 (3%) | H1 | HB3 | 5.5 | 4.6 | Blue | 120 |
| D1 (3%) | H3 | HB3 | 5.8 | 4.8 | Blue | 135 |
| C19 (5%) | H1 + SH2 | HB3 | 4.2 | 6.5 | Blue | 480 |
| C19 (5%) | H4 + SH3 | HB3 | 4.0 | 6.8 | Blue | 440 |
| C18 (15%) | H5 | TPBi | 7.5 | 8.8 | Blue | 24 |
| C18 (15%) | H5 | TPBi | 8.0 | 10.5 | Blue | 8 |

In the above preferred embodiments for organic EL device test report (see Table 1), we show that the light emitting material with a general formula (1) used as emitting dopant material for organic EL in the present invention display good performance than the prior art of organic EL materials. More specifically, the organic EL device in the present invention use the light emitting material with a general formula (1) as emitting guest material to collocate with emitting host material such as H1, H2, H3 and H4 shown lower power consumption, higher efficiency and longer half-life time. Besides we utilize SH1 to SH4 as second host to co-deposit with H1 to H4 shown the best efficiency and half-life time than others.

To sum up, the present invention discloses a light emitting material with a general formula (1) used as emitting dopant material for organic EL device. The mentioned light emitting material are represented by the following formula (1)

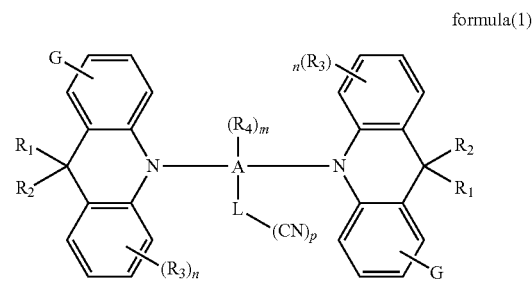

formula(1)

wherein G represents the following formula (2):

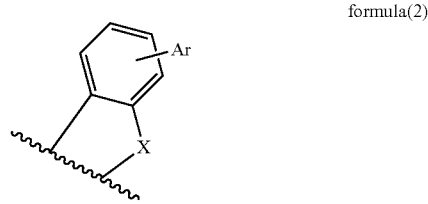

formula(2)

A represents a fused ring hydrocarbon units with two to five rings, provided A represents a naphthyl group, a phenanthrenyl group, a anthracenyl group, a pyrenyl group, a chrysenyl group, a triphenylenyl group and a perylenyl group; L represents a single bond, a substituted or unsubstituted phenylene group or a substituted or unsubstituted heterophenylene group, X represents a divalent bridge selected from the atom or group consisting from O, S, C(R$_5$)(R$_6$), Si(R$_7$)(R$_8$) and N(R$_9$), Ar represents a fused carbocyclic ring or R$_1$, m represents an integer of 0 to 10, n represents an integer of 0 to 4, p represents an integer of 0 to 4, R$_1$ to R$_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:
1. A organic electroluminescence device comprising a pair of electrodes consisting of a cathode and an anode, and between the pairs of electrodes comprising at least a light emitting layer, one or more layers of organic thin film layer, wherein the light emitting layer comprising the light emitting material represented by the following formula (1):

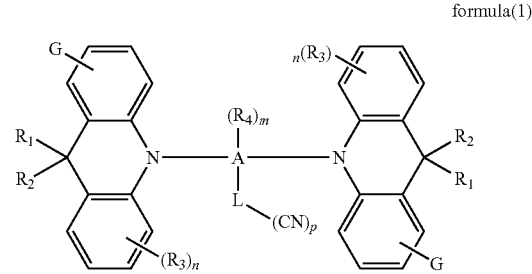

formula(1)

wherein G represents the following formula (2):

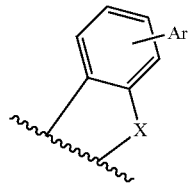

formula(2)

A represents a naphthyl group, a phenanthrenyl group, a anthracenyl group, a pyrenyl group, a chrysenyl group, a triphenylenyl group or a perylenyl group; L represents a single bond, a substituted or unsubstituted phenylene group or a substituted or unsubstituted heterophenylene group, X represents a divalent bridge selected from the atom or group consisting from O, S, C($R_5$)($R_6$), Si($R_7$) ($R_8$) and N($R_9$), Ar represents a fused carbocyclic ring or $R_1$, m represents an integer of 0 to 10, n represents an integer of 0 to 4, p represents an integer of 0 to 4, $R_1$ to $R_9$ are independently selected from the group consisting of a hydrogen atom, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms;

wherein the light emitting layer comprises a fluorescence host material having one of the following formulas:

H1
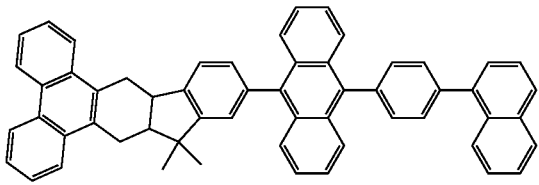

H2
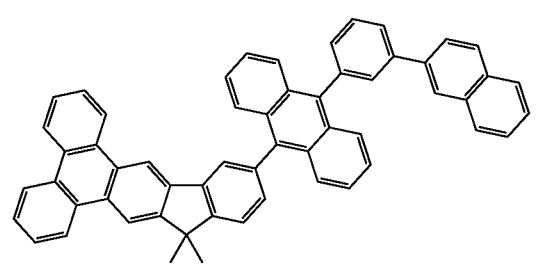

H3
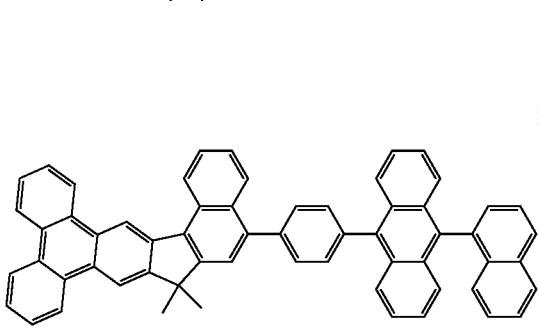

H4
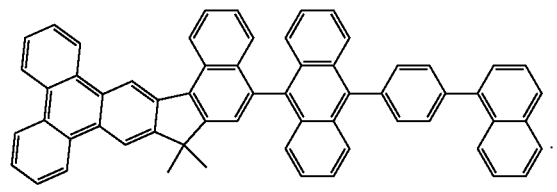

2. The organic electroluminescence device according to claim 1, wherein the light emitting layer comprising the light emitting material with a general formula (1) is a fluorescence dopant material.

3. The organic electroluminescence device according to claim 1, wherein the light emitting layer comprising the light emitting material with a general formula (1) is a delayed fluorescence dopant material.

4. The organic electroluminescence device according to claim 1, wherein the light emitting layer comprising a second fluorescence dopant material.

5. The organic electroluminescence device according to claim 1, wherein the light emitting layer comprising a second fluorescence host material.

6. The organic electroluminescence device according to claim 1, wherein the device is an organic light emitting device.

7. The organic electroluminescence device according to claim 1, wherein the device is a lighting panel.

8. The organic electroluminescence device according to claim 1 wherein the device is a backlight panel.

9. The organic electroluminescence device according to claim 5, wherein the second fluorescence emitting host comprising the following formulas:

SH1
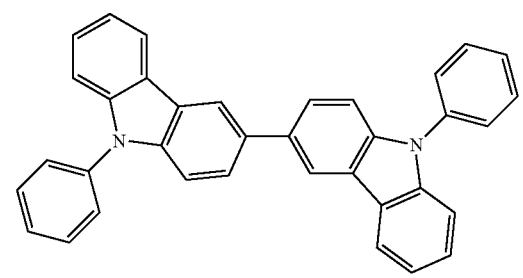

SH2
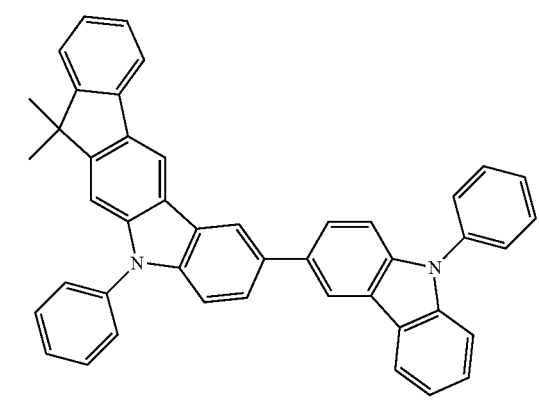

-continued
SH3
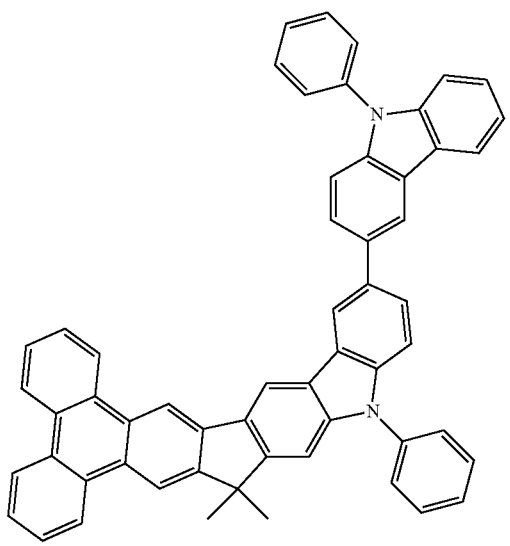
-continued
SH4
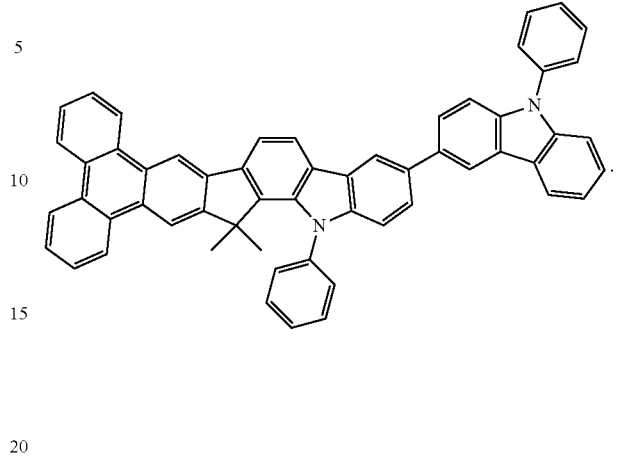
* * * * *